United States Patent
Chen et al.

(10) Patent No.: US 11,510,854 B2
(45) Date of Patent: Nov. 29, 2022

(54) HAIR CARE COMPOSITION

(71) Applicant: Conopeo, Inc., Englewood Cliffs, NJ (US)

(72) Inventors: Guoqiang Chen, Shanghai (CN); Michael John Hoptroff, Birkenhead (GB); Chengdong Ji, Shanghai (CN); Miao Miao, Sichuan (CN); Qiang Zhao, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/492,999

(22) PCT Filed: Mar. 12, 2018

(86) PCT No.: PCT/EP2018/056061
§ 371 (c)(1),
(2) Date: Sep. 11, 2019

(87) PCT Pub. No.: WO2018/172121
PCT Pub. Date: Sep. 27, 2018

(65) Prior Publication Data
US 2020/0016054 A1    Jan. 16, 2020

(30) Foreign Application Priority Data

Mar. 23, 2017 (WO) ............... PCT/CN2017/077921
May 10, 2017 (EP) ..................... 17170471

(51) Int. Cl.
| | |
|---|---|
| A61K 8/27 | (2006.01) |
| A61K 8/49 | (2006.01) |
| A61K 8/898 | (2006.01) |
| A61K 8/46 | (2006.01) |
| A61K 8/37 | (2006.01) |
| A61K 8/35 | (2006.01) |
| A61Q 5/02 | (2006.01) |

(52) U.S. Cl.
CPC .................. *A61K 8/27* (2013.01); *A61K 8/35* (2013.01); *A61K 8/37* (2013.01); *A61K 8/463* (2013.01); *A61K 8/4933* (2013.01); *A61K 8/898* (2013.01); *A61Q 5/02* (2013.01)

(58) Field of Classification Search
CPC ....................................................... A61K 8/27
See application file for complete search history.

(56) References Cited

U.S. PATENT DOCUMENTS

| | | | |
|---|---|---|---|
| 5,939,203 | A | 8/1999 | Kappock et al. |
| 2004/0028642 | A1 | 2/2004 | Hansenne et al. |
| 2004/0213751 | A1 | 10/2004 | Schwartz et al. |
| 2004/0253194 | A1* | 12/2004 | Rioux ................. C10M 141/12 424/70.11 |
| 2006/0165616 | A1 | 7/2006 | Brock et al. |
| 2006/0248663 | A1 | 11/2006 | Tremblay et al. |
| 2008/0025929 | A1 | 1/2008 | Burton et al. |
| 2009/0169644 | A1* | 7/2009 | Goddinger ............. A61K 8/922 424/642 |
| 2009/0246156 | A1 | 10/2009 | Kunin |
| 2010/0119461 | A1 | 5/2010 | Bicard-Benhamou et al. |
| 2010/0278763 | A1 | 11/2010 | Loeffler et al. |
| 2012/0058057 | A1 | 3/2012 | Pitner et al. |
| 2016/0015615 | A1 | 1/2016 | Mann et al. |

FOREIGN PATENT DOCUMENTS

| | | |
|---|---|---|
| CN | 104994913 | 10/2015 |
| DE | 102010063791 | 9/2011 |
| EA | 1923043 | 5/2008 |
| EP | 1604640 | 12/2005 |
| EP | 2939710 | 11/2015 |
| JP | S52092881 | 8/1977 |
| JP | 2003503333 | 1/2003 |
| JP | 2006519769 | 8/2006 |
| JP | 2016507563 | 3/2016 |
| WO | WO9913844 | 3/1999 |
| WO | WO0100151 | 1/2001 |
| WO | WO0239974 | 5/2002 |
| WO | WO2004082649 | 9/2004 |
| WO | WO2007075747 | 5/2007 |
| WO | WO2014124068 | 8/2014 |
| WO | WO2014124070 | 8/2014 |
| WO | WO2015198338 | 12/2015 |
| WO | WO2010/040671 | * 7/2020 |

OTHER PUBLICATIONS

Search Report and Written Opinion in EP17170471; dated Jul. 27, 2017.
Search Report and Written Opinion in PCTEP2018056061; dated May 11, 2018.
Mintel GNPD; Shampoo; L'Oreal Elseve Color-Vive; Sep. 2011; Record ID 1620719, pp. 1-2; Czech Republic.
Mintel GNPD; Anti-Dandruff Beauty Shampoo; L'Oreal Elseve Color-Vive; Oct. 2010 Record II 1425537, pp. 1-2; Belgium.
Mintel GNPD; Anti-Dandruff Beauty Shampoo; L'Oreal Elseve Color-Vive; Oct. 2010 Record ID 1405868, pp. 1-2; Switzerland.
Mintel GNPD; Beauty Shampoo; L'Oreal Elseve Color-Vive; Mar. 2010; Record ID 1281335, pp. 1-2; France.
Mintel GNPD; Colour Shine Shampoo; L'Oreal Elvital Anti-Dandruff; Feb. 2010 Record 1266018, pp. 1-2; Germany.

(Continued)

*Primary Examiner* — Sarah Alawadi
(74) *Attorney, Agent, or Firm* — Foley & Lardner LLP

(57) ABSTRACT

This invention relates to a hair care composition more particularly to a wash-off composition, especially preferred being a shampoo or a conditioner, which provides the desired anti-dandruff efficacy with enhanced stability of the active materials on hair/scalp during use. This is achieved through a judicious combination of an organic UV filter, a zinc compound and selective anti-dandruff agent. The composition comprises 0.01 to 3% by weight zinc pyrithione, an organic UV filter and 0.1 to 5% by weight additional zinc compound. The weight ratio of zinc compound to zinc pyrithione is over 3:1.

13 Claims, No Drawings

(56) References Cited

OTHER PUBLICATIONS

Mintel GNPD; Sensitive Scalp Shampoo; Define; Jul. 2008; Record ID 940160, pp. 1-2; Norway.
Mintel GNPD; Anti-Dandruff Shampoo; Carin; Oct. 2006; Record ID 602594, pp. 1-2; Israel.
Mintel GNPD; Conditioner; Style Aromatherapy Pro Haircare Anti-Dandruff; Nov. 2011; Record ID 1662871, pp. 1-2; Singapore.
Mintel GNPD; Conditioner; Style Aromatherapy Pro Haircare Anti-Dandruff; Sep. 2011; Record ID 1623740, pp. 1-2; Israel.

* cited by examiner

HAIR CARE COMPOSITION

CROSS REFERENCE TO RELATED APPLICATIONS

The present application is a U.S. National Phase Application under 35 U.S.C. § 371 of International Application No. PCT/EP2018/056061, filed on Mar. 12, 2018, which claims priority to International Application No. PCT/CN2017/077921, filed on Mar. 23, 2017, and Chinese patent application No. 17170471.1 filed on May 10, 2017, the contents of which are incorporated by reference herein in their entireties.

FIELD OF THE INVENTION

This invention relates to a hair care composition which provides desired anti-dandruff efficacy with optimum stability of the active materials on hair/scalp to ensure maximum anti-dandruff efficacy. The composition may be delivered as a wash off composition, e.g. a shampoo or a hair conditioner.

BACKGROUND OF THE INVENTION

Hair care compositions generally provide cleansing or conditioning benefits or a combination of the two. Such compositions typically comprise one or more cleansing surfactants which generally aid in cleaning the hair and/or the scalp free of undesirable soil, particles and fatty matter. Conditioning benefit is achieved by including one or more conditioning agents in the hair care composition. Conditioning benefit is delivered with an oily material being deposited onto the hair resulting in the formation of a film, which makes the hair easier to comb when wet and more manageable when dry.

Additionally, anti-dandruff benefit has been provided through hair care compositions, both through shampoos and through hair conditioners. Dandruff is an issue that affects many people globally. The condition is manifested by the shedding of clumps of dead skin cells from the scalp. These are white in colour and provide an aesthetically displeasing appearance. A factor that is believed to contribute to dandruff is certain members of the *Malassezia* yeasts. To combat these, anti-dandruff products have included certain zinc salts which have anti-fungal activity, for example zinc pyrithione (ZPTO). Such a product has to perform as a hair cleansing shampoo or as a hair conditioner, while mitigating the ill-effects of dandruff. Typical anti-dandruff agents used in hair care are metal pyrithione e.g zinc pyrithione (ZPTO), octopirox (piroctone olamine), azole antimicrobials (e.g. climbazole), selenium sulfide and combinations thereof.

Many antidandruff hair care products presently comprise zinc based antidandruff agents like zinc pyrithione (ZPTO, which is a particulate agent). It is found that dissolved intact ZPTO molecules are the sole bioactive form of ZPTO. When hair care product with a zinc based anti-dandruff agent like ZPTO is utilized, there is the so-called ZPTO dissociation and photo-oxidation problem where the stability of the bioactive is compromised with the formation of zinc salts which can lower the antidandruff efficacy. US 20040213751A1 (2004, P&G) discloses a composition comprising: a) an effective amount of pyrithione or a polyvalent metal salt of a pyrithione; b) an effective amount of a zinc-containing layered material which provides an augmentation factor greater than 1.

WO2015/198338A1 (2015, Jubilant Life Science LTD) discloses a synergistic antimicrobial composition comprising zinc pyrithione and zinc salt of pyridine carboxylic acid.

WO 01/00151 A1 (2001, P&G; Arch Chem Inc) discloses a topical composition for the treatment of microbial infections on the skin or scalp which include a polyvalent metal salt of pyrithione and include a metal ion source.

The present invention relates to utilization of ZPTO in the hair care products and to improve the stability of the bioactive. The present inventors, during the course of identifying stabilizers which would protect the dissolved intact ZPTO molecules from photo-oxidation and dissociation, have identified the specific combination of a class of organic UV filters and selective zinc compound which could be used to inhibit the photo-oxidation and dissociation of ZPTO, and provide further enhanced stabilization of the ZPTO bioactive. Shampoo comprising ZPTO and UV filters have been in the market. They generally combine them with Zn sulphate which is usually included at very low concentration. The present inventors have found that when zinc compound is included at higher than 0.1% weight percentage with the weight ratio of zinc compound to ZPTO of at least 1:1, could have the synergistic effect with organic UV filters for improving the stability of the ZPTO bioactive.

It is thus an object of the present invention to enhance the stability of the zinc based anti-dandruff bioactive.

SUMMARY OF THE INVENTION

According to the first aspect of the present invention there is provided a hair care composition comprising from
(i) 0.01 to 3% by weight zinc pyrithione;
(ii) an organic UV filter; and
(iii) 0.1 to 5% by weight additional zinc compound,
wherein the weight ratio of zinc compound to zinc pyrithione is over 3:1.

According to the second aspect of the present invention there is provided a non-therapeutic method of improving the stability of a zinc based antidandruff agent on to scalp comprising the steps of applying a composition of the first aspect on to the desired surface followed by rinsing the surface with water.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. In other words, in specifying any ranges of values, any particular upper value can be associated with any particular lower value.

The disclosure of the invention, as found herein, is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

By 'A Hair Care Composition" as used herein, is meant to include a composition for topical application to hair and/or scalp of mammals, especially humans. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, or bar. Non-limiting examples of such compositions include leave-on hair lotions, creams, and wash-off shampoos, conditioners, shower gels, or toilet bar. The composition of the present invention is preferably a wash-off composition, especially preferred being a shampoo or a conditioner.

The present invention relates to a hair care composition comprising 0.01 to 3% zinc pyrithione; an organic UV filter; and 0.1 to 5% additional zinc compound, wherein the weight ratio of zinc compound to zinc pyrithione is over 3:1.

Zinc pyrithione belongs to the class of insoluble metal pyrithione which may be represented by the following general formula:

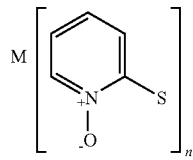

in which M is a polyvalent metal ion and n corresponds to the valency of M. In the present invention M corresponds to Zinc and n has the value of 2.

The zinc pyrithione may have any particle form suitable for use in a composition for topical application. For example, the zinc pyrithione may be in the form of amorphous or crystalline particles having a range of different particle sizes. The zinc pyrithione may, for example, be in the form of particles having a size distribution in which at least about 90% of the particles have a size of up to 100 microns, more preferably up to 50 microns, even more preferably up to 10 microns, most preferably 5 microns or less.

Various methods for producing fine particles of metal pyrithione are described, for example, in EP-A-0 173 259. Suitable methods for determining particle size are described in that document. The insoluble metal pyrithione may be made up of one particulate form or two or more different particulate forms.

Other suitable particulate forms for the zinc pyrithione include platelets and needle-shaped particles. Platelets of zinc pyrithione are described in EP-A-0034385, the contents of which are incorporated herein by reference. The needle shaped particles are preferably of the type described in WO99/66886, the contents of which are incorporated herein by reference. For needle-shaped particles preferably at least 50% by number of the particles are needle-shaped particles having a length of between 1 μm and 50 μm.

The amount of metal pyrithione incorporated into the compositions may depend on the type of composition and the exact nature of the material used. A preferred amount of pyrithione is from 0.01 to 3%, more preferably from about 0.01 to 1.5% by weight of the total composition, furthermore preferably from 0.05 to 1.5% by weight of the total composition.

Organic UV filters are individual compounds or mixtures that absorb ultraviolet (UV) light. ZPTO bioactive is not stable and breaks into zinc ion, pyrithione (PT) and other by-products through photo-degradation. The inventors expect that with the use of organic UV filter in the composition as per the invention, the anti-dandruff efficacy is expected to be enhanced through maximizing the active stability.

The organic UV filter as per the invention is selected from a wide variety of organic UV filter which is suitable for use in combination with the essential ingredients of this invention. Suitable UV-A/UV-B or UVA+UVB filter include, 2-hydroxy-4-methoxybenzophenone, octyldimethyl p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, octyldimethyl-p-aminobenzoic acid, butylmethoxydibenzoylmethane, 2-hydroxy-4-methoxybenzophenone, bisdisulizole disodium, phenylbenzimidazole sulfonic acid, octyl methoxycinnamate, bemotrizinol, bisoctrizole and mixtures thereof.

Preferably the organic UV filter as per the invention is selected from bisdisulizole disodium, 2-hydroxy-4-methoxybenzophenone, butyl methoxydibenzoylmethane, phenylbenzimidazole sulfonic acid, octyl methoxycinnamate, bemotrizinol and bisoctrizole. The most suitable organic UV filters are butyl methoxydibenzoylmethane and octyl methoxycinnamate.

The amount of organic UV filter incorporated into the compositions may depend on the amount of zinc based anti-dandruff agent used. A preferred amount of organic UV filter is from 0.1 to 15%, most preferably from 1 to 15% by weight of the total composition.

The composition as per the invention comprises an additional zinc compound. The presence of zinc compound in the composition is believed to have ability to synergistically stabilize ZPTO bioactive in the presence of an organic UV filter. Thus, as a first essential component there is required a compound, especially a salt, delivering zinc ions. By the term "zinc ion" is meant that the zinc-atom portion of a molecule of the zinc compound in the solid or undissociated state, is capable of being dissociated into simple or complex zinc ions, especially when dispersed in an aqueous medium. Examples of the compounds that may be employed are zinc oxide and zinc salts of the following inorganic ions: borate, bromide, carbonate, hexafluorosilicate, pyrophosphate, silicate, sulphate and titanate. Specific examples include, but are not limited to, zinc oxide, zinc acetate, zinc chloride, zinc citrate, and carbonate.

The amount of zinc compound incorporated into the compositions may depend on the amount of zinc based anti-dandruff agent used and type of composition. A preferred amount of zinc compound is from 0.1 to 5%, more preferably from 1 to 5% by weight of the total composition. The weight ratio of zinc compound to zinc pyrithione is over 3:1, preferably over 5:1.

As per an especially preferred aspect of the invention, the composition is a shampoo or conditioner.

The composition of the invention especially shampoos are formulated preferably with an anionic surfactant e.g. an alkyl sulphate and/or ethoxylated alkyl sulfate surfactant. These anionic surfactants are preferably present at a level of from 2 to 16%, more preferably from 3 to 16% by weight of the composition. Preferred alkyl sulfates are C8-18 alky sulfates, more preferably C12-18 alkyl sulfates, preferably in the form of a salt with a solubilising cation such as sodium, potassium, ammonium or substituted ammonium. Examples are sodium lauryl sulfate (SLS) or sodium dodecyl sulfate (SDS).

Preferred alkyl ether sulfates are those having the formula: RO($CH_2CH_2O$)$_n$SO$_3$M; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES).

Preferred ethoxylated alkyl sulfate anionic surfactant is sodium lauryl ether sulfate (SLES) having an average degree of ethoxylation of from 0.5 to 3, preferably 1 to 3.

The composition as per the invention optionally and preferably additionally comprises a betaine surfactant. In a preferred embodiment, the composition comprises from 0.1 to 10 wt. %, preferably from 0.5 to 8 wt. %, more preferably from 1 to 5 wt. % of a betaine surfactant, preferably an alkyl amidopropyl betaine, for example cocamidopropyl betaine.

Shampoo compositions according to the invention may comprise one or more further anionic cleansing surfactants which are cosmetically acceptable and suitable for topical application to the hair.

Examples of further suitable anionic cleansing surfactants are the alkaryl sulphonates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in shampoo compositions of the invention include sodium oleyl succinate, ammonium lauryl sulphosuccinate, sodium lauryl ether sulphosuccinate, sodium dodecylbenzene sulphonate, triethanolamine dodecylbenzene sulphonate, lauryl ether carboxylic acid and sodium N-lauryl sarcosinate.

Suitable preferred additional anionic cleansing surfactants are sodium lauryl ether sulphosuccinate(n)EO, (where n is from 1 to 3), lauryl ether carboxylic acid (n) EO (where n is from 10 to 20).

Mixtures of any of the foregoing anionic cleansing surfactants may also be suitable.

If added, the total amount of anionic cleansing surfactant in shampoo compositions of the invention may generally range from 0.5 to 45 wt. %, preferably from 1.5 to 35 wt. %, more preferably from 5 to 20 wt. %, calculated by total weight anionic cleansing surfactant based on the total weight of the composition.

The hair conditioning composition comprises conditioning surfactants selected from cationic surfactants, used singly or in admixture. Preferably, the cationic surfactants have the formula N+R1R2R3R4 wherein R1, R2, R3 and R4 are independently (C1 to C30) alkyl or benzyl. Preferably, one, two or three of R1, R2, R3 and R4 are independently (C4 to C30) alkyl and the other R1, R2, R3 and R4 group or groups are (C1-C6) alkyl or benzyl. More preferably, one or two of R1, R2, R3 and R4 are independently (C6 to C30) alkyl and the other R1, R2, R3 and R4 groups are (C1-C6) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (eg, oleyl). Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant. Yet another preferred cationic surfactant is stearamidopropyl dimethylamine.

The most preferred cationic surfactants for use in the composition are stearamidopropyl dimethylamine, behentrimonium chloride, or stearyl trimethyl ammonium chloride. In conditioners of the invention, the level of cationic surfactant will generally range from 0.1 to 5%, preferably 0.5 to 2.5% by weight of the composition.

Hair conditioning compositions of the invention preferably may also additionally comprise a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.5 to 10%, preferably from 0.1 to 8%, more preferably from 0.2 to 7%, most preferably from 0.3 to 6% by weight of the composition. The weight ratio of cationic surfactant to fatty alcohol is suitably from 1:1 to 1:10, more preferably from 1:1.5 to 1:8, optimally from 1:2 to 1:5.

According to another aspect of the invention there is provided a non-therapeutic method of improving the stability of a zinc-based antidandruff agent on to scalp with comprising the steps of applying a composition of the invention on to the desired surface followed by rinsing the surface with water.

The invention will now be illustrated with reference to the following non-limiting Examples.

EXAMPLES

Example 1-7: Effect of the Combination of Organic UV Filter and Zinc Compound as Per the Invention on the Stability of ZPTO Bioactive The following compositions having the specific combination of organic UV filter and zinc acetate as shown in Table-1 were prepared.

TABLE 1

| Components | Zinc pyrithione wt % | Organic UV filters wt % | Type of organic UV filters | Zinc acetate wt % | Water and methanol (1:1) wt % |
|---|---|---|---|---|---|
| EX A | 0.002 | 0 | — | 0 | To 100 |
| EX B | 0.002 | 0 | — | 0.11 | To 100 |
| EX C | 0.002 | 0.14 | a | 0 | To 100 |
| EX 1 | 0.002 | 0.14 | a | 0.11 | To 100 |
| EX D | 0.002 | 0.31 | b | 0 | To 100 |
| EX 2 | 0.002 | 0.31 | b | 0.11 | To 100 |
| EX E | 0.002 | 0.33 | c | 0 | To 100 |
| EX 3 | 0.002 | 0.33 | c | 0.11 | To 100 |
| EX F | 0.002 | 0.34 | d | 0 | To 100 |
| EX 4 | 0.002 | 0.34 | d | 0.11 | To 100 |
| EX G | 0.002 | 0.11 | e | 0 | To 100 |
| EX 5 | 0.002 | 0.11 | e | 0.11 | To 100 |
| EX H | 0.002 | 0.15 | f | 0 | To 100 |
| EX 6 | 0.002 | 0.15 | f | 0.11 | To 100 |
| EX I | 0.002 | 0.16 | g | 0 | To 100 |
| EX 7 | 0.002 | 0.16 | g | 0.11 | To 100 | a—Phenylbenzimidazole sulfonic acid; b—Bemotrizinol; c—Bisoctrizole; d—Bisdisulizole disodium; e—2-hydroxy-4-methoxybenzophenone; f—Octyl methoxycinnamate; g—Butyl methoxydibenzoylmethane.

The compositions in Table-1 above were subjected to a procedure that gives an estimate of the residual amount of $Zn(PT)_2$ active in the hair care composition after being exposed to UV light for long time. The % average residue of $Zn(PT)_2$ was measured using an in vitro model as given below.

Test Condition—UV Light Model:

The UV irradiation was carried out in an X-Rite (Macbeth) Spectra Light III chamber. UV mode was chosen for UV irradiation which provides both UVA and UVB lights. The UV intensity was fixed by the machine (estimated at 250 µw/cm² for UVA and 110 µw/cm² for UVB). The transmittance of UVA and UVB in glass vial was 80.3% and 71.9%, respectively. The chamber temperature was equal to the room temperature (20±2° C.). The samples were placed in a line close to the center of the chamber. 1 hour, 2 hours and 3 hours of irradiation were compared for screening $Zn(PT)_2$ stabilizers.

Test procedure: After preparation, the samples were placed in UV light chamber for a period of irradiation (t=1, 2, 3, 4 hours). Afterwards, at different time points the changes of intact $Zn(PT)_2$ in samples were quantitatively measured using UPLC-UV analysis following DPS derivatization.

DPS derivation: At different time points, 1 mL of solution was taken from each sample for analysing the amount of intact $Zn(PT)_2$. The solution was firstly diluted with 1 mL of methanol, and then equally separated into 2 parts for parallel analysis. Each part of solution was mixed with 100 µL of saturated EDTA-2Na and 250 µL of DPS reagent, and then placed in dark for the derivatization of $Zn(PT)_2$. After 30 minutes of derivatization, the solution was filtered and subjected to HPLC-UV analysis.

A Waters ACQUITYUPLC System coupled to a Quattro Micro API mass spectrometer (Waters, Manchester, UK) was used for the sample analysis. Separation was carried out on a Waters Acquity UPLC BEH C18 column (2.1 mm×50 mm×1.7 µm). The mobile phase was composed of 20 mM ammonium acetate in water and methanol programmed in the linear gradient mode. Atmospheric pressure chemical ionization (APCI) in positive mode was used for all experiments. The multiple reaction monitoring (MRM) mode was used for the determination of $Zn(PT)_2$.

The data of stability of ZPTO in the composition of Table-1 is listed in table-2 below.

TABLE 2

| Stability test of ZPTO | % average[1] residue of $Zn(PT)_2$ 1 h | SD [2] | % average residue of $Zn(PT)_2$ 2 h | SD | % average residue of $Zn(PT)_2$ 3 h | SD |
|---|---|---|---|---|---|---|
| EX A | 41.0 | 1.3 | 15.4 | 0.4 | 8.3 | 0.1 |
| EX B | 67.9 | 0.7 | 29.9 | 0.4 | 14.5 | 1.5 |
| EX C | 13.4 | 0.2 | 12.8 | 0.9 | 10.3 | 0.4 |
| EX 1 | 62.0 | 11.7 | 38.0 | 0.2 | 24.0 | 0.2 |
| EX D | 67.4 | 0.2 | 41.3 | 0.3 | 34.2 | 12.4 |
| EX 2 | 81.8 | 1.5 | 57.6 | 1.8 | 52.2 | 3.7 |
| EX E | 83.0 | 4.1 | 40.8 | 3.3 | 34.2 | 1.9 |
| EX 3 | 81.5 | 2.8 | 53.9 | 2.5 | 55.7 | 2.5 |
| EX F | 61.6 | 0.3 | 40.6 | 1.6 | 36.5 | 3.4 |
| EX 4 | 71.0 | 10.3 | 69.6 | 1.9 | 64.3 | 5.3 |
| EX G | 100.0 | 6.2 | 69.4 | 0.4 | 69.7 | 1.7 |
| EX 5 | 100.0 | 1.4 | 72.8 | 1.6 | 77.6 | 9.6 |
| EX H | 97.4 | 0.5 | 92.7 | 2.0 | 89.5 | 0.9 |
| EX 6 | 97.3 | 0.5 | 96.7 | 1.1 | 93.5 | 1.1 |
| EX I | 100.0 | 1.1 | 98.9 | 1.1 | 96.7 | 1.1 |
| EX 7 | 100.0 | 0.6 | 100.0 | 0.6 | 96.1 | 0.5 |

[1] It indicates the average of two readings.
[2] SD is the standard deviation of the % average residue.

The data above indicates that compositions as per the invention (Examples 1 to 7) provide for better ZPTO bioactive stability as compared to a corresponding example outside the invention (Examples C to I, not containing the additional zinc compound) after being exposed to light for longer than 1 hour.

Example 8: Effect of a Different Zinc Compound (Zinc Chloride) as Per the Invention on the Stability of ZPTO Bioactive The following compositions having the specific combination of organic UV filter and zinc chloride as shown in Table-3 were prepared.

TABLE 3

| Components wt % | Zinc pyrithione wt % | 2-hydroxy-4-methoxybenzophenone wt % | Zinc chloride wt % | Water and methanol (1:1) wt % |
|---|---|---|---|---|
| EX J | 0.002 | 0 | 0 | To 100 |
| EX K | 0.002 | 0 | 0.007 | To 100 |
| EX L | 0.002 | 0.01 | 0 | To 100 |
| EX 8 | 0.002 | 0.01 | 0.007 | To 100 |

The ZPTO residues of the various compositions were measured using an in vitro model as given herein above. The data of stability of ZPTO in the composition of Table-3 is listed in Table-4 below.

TABLE 4

| Stability test of ZPTO | % average residue of $Zn(PT)_2$ 1 h | SD | % average residue of $Zn(PT)_2$ 3 h | SD |
|---|---|---|---|---|
| EX J | 41.2 | 0.6 | 8.1 | 0.6 |
| EX K | 58.0 | 2.0 | 18.3 | 0.1 |
| EX L | 93.2 | 0.7 | 75.2 | 0.6 |
| EX 8 | 95.5 | 1.5 | 86.5 | 1.4 |

The data in Table-4 above indicates that composition as per the invention (Example 8) provides for better ZPTO stability as compared to examples outside the invention (Examples J to L).

Example 9: Effect of the Ratios of Organic UV Filter and Zinc Compound Vs ZPTO in the Composition as Per the Invention on the Stability of ZPTO Bioactive The following compositions having the specific combination of organic UV filter and zinc acetate as shown in Table-5 were prepared. The ZPTO residues of the various compositions were measured using an in vitro model as given herein above. The data of stability of ZPTO in the composition is also listed in Table-5.

TABLE 5

| Components, wt % | Zinc pyrithione wt % | Organic UV filters (Octyl methoxycinnamate) wt % | Zinc acetate wt % | Weight ratio (zinc compound:zinc pyrithione) | Water and methanol (1:1) wt % | % average residue of $Zn(PT)_2$ 1 h | SD |
|---|---|---|---|---|---|---|---|
| EX M | 0.002 | 0 | 0 | — | To 100 | 10.62 | 0.60 |
| EX N | 0.002 | 0 | 0.0002 | 1:10 | To 100 | 10.38 | 0.47 |
| EX O | 0.002 | 0.0002 | 0.0002 | 1:10 | To 100 | 11.1 | 0.47 |
| EX P | 0.002 | 0.002 | 0.0002 | 1:10 | To 100 | 17.68 | 0.12 |
| EX Q | 0.002 | 0.01 | 0.0002 | 1:10 | To 100 | 28.85 | 0.20 |
| EX 9 | 0.002 | 0.01 | 0.01 | 5:1 | To 100 | 41.43 | 0.72 |

The data above indicates that composition as per the invention (Examples 9) provides for better ZPTO bioactive stability as compared to an example outside the invention (Examples M to Q).

Example 10-13: Effect of the Ratios of Zinc Compound Vs ZPTO in the Composition as Per the Invention on the Stability of ZPTO Bioactive The following compositions having the specific combination of organic UV filter and zinc acetate as shown in Table-6 were prepared. The ZPTO residues of the various compositions were measured using an in vitro model as given herein above. The data of stability of ZPTO in the composition is also listed in Table-6.

TABLE 6

| | Zinc pyrithione | Organic UV filter | Zinc compound | Zinc compound wt % | Weight ratio | Water and methanol (1:1) | % average residue | SD |
|---|---|---|---|---|---|---|---|---|
| EX R | 0.002 | 0 | | 0 | | To 100 | 2.94 | 0.02 |
| EX S | 0.002 | 0.002 | ZnO | 0.002 | 1:1 | To 100 | 13.40 | 0.25 |
| EX T | 0.002 | 0.002 | | 0.003 | 1.5:1 | To 100 | 14.10 | 0.05 |
| EX 10 | 0.002 | 0.002 | | 0.007 | 3.5:1 | To 100 | 14.80 | 0.1 |
| EX 11 | 0.002 | 0.002 | | 0.01 | 5:1 | To 100 | 15.85 | 0.15 |
| EX U | 0.002 | 0.002 | ZnAc | 0.002 | 1:1 | To 100 | 20.15 | 0.05 |
| EX V | 0.002 | 0.002 | | 0.003 | 1.5:1 | To 100 | 22.55 | 0.10 |
| EX 12 | 0.002 | 0.002 | | 0.007 | 3.5:1 | To 100 | 26.75 | 0.10 |
| EX 13 | 0.002 | 0.002 | | 0.01 | 5:1 | To 100 | 28.25 | 0.05 |

The data above indicates that composition as per the invention (Examples 10 to 13) provides for better ZPTO bioactive stability as compared to an example outside the invention (Examples R to V). The data clearly indicates that stability of ZPTO bioactive increases as the ratios of zinc compound vs ZPTO in the composition is increased with same zinc compound.

It is to be understood that the experiments described above were conducted in a test tube at concentration level needed to prove that it is essential to combine zinc pyrithione, organic UV filter and additional zinc compound to get the desired stability benefit. It is expected that the concentrations to be actually used to prepare a composition for topical use would be vastly different. The concentrations could be orders of magnitude higher due to reasons that affect the difference in concentration in the bulk as compared to that at the cellular level. The composition may be formulated as an emulsion or a gel with very many additional ingredients which affect the concentration of the desired actives—e.g. a water insoluble material like ZPTO, an oily or particulate material like an UV filter or a salt/oxide like a zinc compound, in the oil phase and in the water phase which is expected to be very different. They may also have very different physical and hydrodynamic properties like partition coefficients, diffusional rates, convective transport rates, rheological properties etc. Therefore, it is expected that the concentrations to be used when formulated as a composition would be very different from that at the cellular level, at which the experiments were carried out.

The invention claimed is:

1. A hair care composition comprising (i) 0.002 to 3% by weight zinc pyrithione; (ii) 0.1 to 15% by weight an organic UV filter; and (iii) 0.1 to 5% by weight additional zinc compound; wherein the weight ratio of the additional zinc compound to zinc pyrithione is from 3.5:1 to 55:1, wherein the additional zinc compound is selected from zinc oxide, zinc acetate, zinc chloride, zinc citrate or zinc carbonate, and wherein said organic UV filter is selected from bisdisulizole disodium, 2-hydroxy-4-methoxybenzophenone, butyl methoxydibenzoylmethane, octyl methoxycinnamate, bemotrizinol and bisoctrizole.

2. The composition of claim 1 comprising 1 to 5% of the additional zinc compound by weight of the composition.

3. The composition of claim 1 wherein the additional zinc compound is selected from zinc oxide, zinc acetate, or zinc chloride.

4. The composition of claim 1 additionally comprising a surfactant.

5. The composition of claim 4 wherein the surfactant is an anionic surfactant or a cationic surfactant.

6. The composition of claim 5 wherein the anionic surfactant is an alkyl sulphate and/or an ethoxylated alkyl sulfate surfactant.

7. The composition of claim 6 additionally comprising a betaine surfactant.

8. The composition of claim 6 wherein the composition is a shampoo.

9. The composition of claim 5 wherein the cationic surfactant is chosen from stearamidopropyl dimethylamine, behentrimonium chloride, or stearyl trimethyl ammonium chloride.

10. The composition of claim 9 additionally comprising 0.5 to 10 wt % of a fatty alcohol.

11. The composition of claim 9 wherein the composition is a hair conditioner.

12. A non-therapeutic method of improving the stability of a zinc pyrithione antidandruff agent on the scalp comprising the steps of applying the composition of claim 1 on to a desired surface followed by rinsing the surface with water.

13. The composition of claim 1 wherein the weight ratio of the additional zinc compound to zinc pyrithione is from 5:1 to 55:1.

* * * * *